United States Patent [19]

Halloran

[11] Patent Number: 5,811,085
[45] Date of Patent: Sep. 22, 1998

[54] SILOXANE CONDITIONERS FOR HAIR

[75] Inventor: Daniel J. Halloran, Midland, Mich.

[73] Assignee: Dow Corning Corporation, Midland, Mich.

[21] Appl. No.: 37,779

[22] Filed: Mar. 26, 1993

Related U.S. Application Data

[63] Continuation of Ser. No. 462,188, Jan. 9, 1990, abandoned.

[51] Int. Cl.⁶ .................. A61K 7/09; A61K 7/07
[52] U.S. Cl. ............ 424/70.2; 424/70.12; 424/78.03
[58] Field of Search ............... 424/70, 71, 72, 424/70.2, 70.12, 78.03

[56] References Cited

U.S. PATENT DOCUMENTS

| | | | |
|---|---|---|---|
| 4,344,763 | 8/1982 | Tolgyesi | 8/127.51 |
| 4,559,227 | 12/1985 | Chandra et al. | 424/70 |
| 4,563,347 | 1/1986 | Starch | 424/70 |
| 4,568,566 | 2/1986 | Tolentino | 427/54.1 |
| 4,597,962 | 7/1986 | Grollier et al. | 424/47 |
| 4,608,270 | 8/1986 | Varaprath | 427/35 |
| 4,749,732 | 6/1988 | Kohl et al. | 524/43 |
| 4,770,873 | 9/1988 | Wolfram et al. | 424/71 |
| 4,861,906 | 8/1989 | Varaprath et al. | 556/419 |
| 4,876,039 | 10/1989 | Lo | 264/4.7 |

OTHER PUBLICATIONS

Stedman's Medical Dictionary, 25th Ed. p. 362.

*Primary Examiner*—Sally Gardner-Lane
*Attorney, Agent, or Firm*—Sharon K. Severance

[57] ABSTRACT

The use of acrylic functional siloxanes in hair treatment is disclosed. Acrylic functional siloxanes can be used as oxidizing agents in perms or formulated into hair care products such as shampoos or conditioners. They may be cured into/onto the hair using catalysts or radiation.

18 Claims, No Drawings

SILOXANE CONDITIONERS FOR HAIR

This is a continuation of application Ser. No. 07/462,188, filed on Jan. 9, 1990, now abandoned.

This invention pertains to acrylic functional siloxanes that are useful in the perming and conditioning of hair. Of particular usefulness are acrylamide, acryloxy and methacryloxy functional siloxanes. Those useful in the perming of hair can be reacted with the hair using mechanisms such as catalyst systems or radiation.

BACKGROUND OF THE INVENTION

Human hair is composed of a protein material known as keratin (K). Hair is permed by breaking or reducing sulfer-sulfer (K—S—S—K) bonds in the hair structure using a reducing agent followed by rinsing the hair with water to form thio functionality on the hair (K—S—H). The hair is then curled into the desired state and oxidized so that it contains new (curled) K—S—S—K bonds.

In the typical perming procedure, the hair is washed, set and treated with a thioglycolate solution to reduce the hair. Upon sufficient reduction the hair is then rinsed and treated with an aqueous hydrogen peroxide solution to oxidize the hair.

The normal reaction that occurs during oxidation is thought to be $$2 \text{ K—S—H} + \text{H}_2\text{O}_2 \rightarrow \text{K—S—S—K} + 2 \text{ H}_2\text{O} \quad \text{(I)}$$

however if (2) K—S—H groups are not present the following reaction is believed to take place

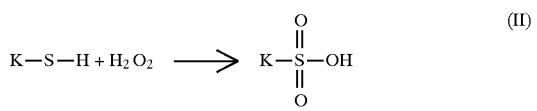

which results in damaged hair. Peroxides are also known to remove non-natural color from hair resulting in further damage. Because of the damage that occurs to the hair, hydrogen peroxides are undesirable as an oxidizing agent in hair perms.

The use of several amine functional silicones in hair care products is known in the art. These amine functional silicones are usually used as additives in the hair care formulations and do not directly replace known products. Through this addition they provide certain beneficial characteristics to the hair.

U.S. Pat. No. 4,559,227 to Chandra et al. teaches the uses of an amine functional methylsiloxane polymer for use in a conditioning shampoo. The amine functional siloxanes taught by Chandra include primary, secondary, and tertiary mono- and di-amines as well as acetamide functionality. The shampoo compositions are shown to cleanse the hair while simultaneously depositing siloxane polymers on the hair to condition.

U.S. Pat. No. 4,563,347 to Starch, teaches a hair conditioning composition which may contain amine functional siloxanes, in particular primary, secondary, tertiary or quarternary amine functionality. It is preferred to use the composition taught by Starch after shampooing. As well as conditioning the hair, the compositions taught also reduce the amount of water retained in the hair thus reducing the time to dry the hair.

U.S. Pat. No. 4,597,962 to Grollier et al., teaches a cosmetic composition for the treatment and care of hair which contains a cationic silicone polymer. The cationic silicone polymer may be amine functional, in particular quarternary amines or Amodimethicone. The compositions, according to Grollier et al., may be applied to the hair in the form of a shampoo, conditioner, setting lotion, permanent wave solution and others.

U.S. Pat. 4,749,732 to Kohl et al., teaches modified aminioalkyl silicones that can be formulated into shampoos, conditioners, rinses, creams, gels, aerosol foams or sprays and permanent waving products. The modification includes an organic ester bonded to the amine group. The hair compositions of this invention allow a higher amount of silicone to be deposited onto the hair.

U.S. Pat. No. 4,4770,873 to Wolfram et al. teaches an oxidizing agent for use in hair perming which comprises a typical oxidizing agent, such as hydrogen peroxide, and an amino-functional polymeric silicone additive. The amine functionality includes primary and secondary amines such as amodimethicone.

This instant invention pertains to the use of acrylic functional siloxanes (ie. acrylamide, methacrylamide, acryloxy and methacryloxy) for use in hair care formulations. Acylamino (acrylamide) functional siloxanes, their preparation and some of their uses are taught, for example, in U.S. Pat. No. 4,608,270 to Varaprath. These compounds are taught to be useful in cosmetic compositions and as a reactive component in free radical curable composition as well as other uses. However, specific cosmetic compositions are not taught and those used as curable compositions are used primarily for sealing, coating encapsulating and molding of various substrates of which hair is not mentioned. The application of using these compounds in hair treatment is not taught nor is it obvious.

Acrylic functional siloxane resin compositions are taught in U.S. Pat. No. 4,568,566 to Toletino. These acrylic functional siloxane resins include inethacryloxy and acryloxy functionality. These acrylic functional siloxane resin compositions are useful as conformal coatings or coatings for optical fibers. Reaction with or on hair is not taught nor is it obvious.

It is an object of this invention to show the use of acrylic functional siloxanes in hair treatment compositions.

It is further an object of this invention to show the use of acrylic functional siloxanes as substitutes for typical oxidizing agents in the perming of hair.

It is further an object of this invention to show the use of acrylic functional siloxanes as additives in shampoo formulations.

THE INVENTION

This invention pertains to the use of acrylic functional siloxanes for hair conditioning and oxidation. Preferred acrylic functional siloxanes of this invention are of the general formulas

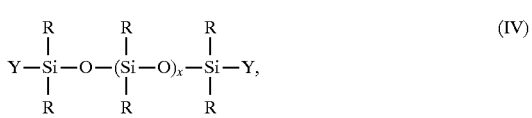

-continued

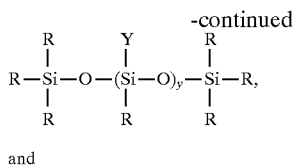

and

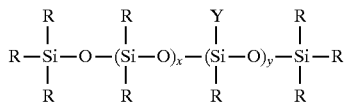

wherein R is independently selected from an alkyl group consisting of 1 to 6 carbon atoms and an aryl group consisting of 6 to 10 carbon atoms; Y is independently selected the groups

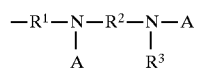

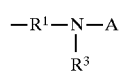

and

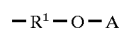

where $R^1$ and $R^2$ are independently selected from straight or branched chain alkylene group consisting of 1 to 10 carbon atoms, and an arylene group consisting of 6 to 10 carbon atoms; any of said $R^1$ and $R^2$ groups optionally containing an ether oxygen or any functional substituent, unreactive with hair, within the aliphatic segments thereof; $R^3$ is selected from the hydrogen atom, an alkyl group of 1 to 10 carbon atoms and an aryl group consisting of 6 to 10 carbon atoms; and A is the group

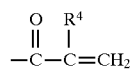

where $R^4$ is selected from the hydrogen atom and methyl group, $CH_3$ (ie. acryl- and methacryl-); x has the value of 1 to 10,000 and y has a value of 1 to 100.

Examples of $R^1$ and $R^2$ include but are not limited to alkylene radicals such as —$CH_2CH_2$—, —$CH_2CH_2CH_2$—, —$CH_2CH(CH_3)CH_2$—, —$(CH_2)_4$—, and arylene radicals such as —$C_6H_4$—, —$CH_2C_6H_4$—and —$CH_2C_6H_4CH_2$—.

$R^3$ may be exemplified by the hydrogen atom, alkyl groups such as methyl, ethyl, propyl, butyl, hexyl, and octyl, and aryl groups such as phenyl, benzyl, styryl, tolyl and xenyl.

The siloxanes of the instant invention include acrylamide, acryloxy and methacryloxy functionality. The preferred embodiments are the acrylainide functional siloxanes in which R is methyl or phenyl, $R^1$ contains at least 3 carbon atoms, $R^2$ is the group —$CH_2CH_2$—and $R^3$ is the hydrogen atom or the methyl group.

The acrylic functional group, Y, may be further exemplified by, but not limited to, the following structures

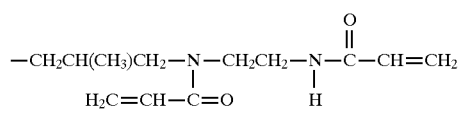

-continued

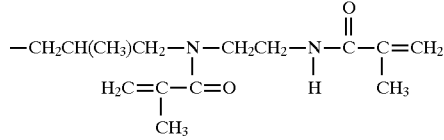

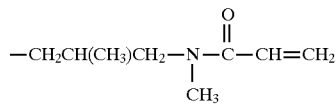

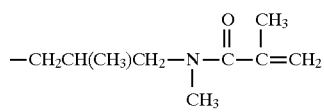

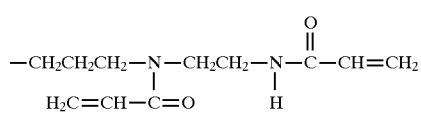

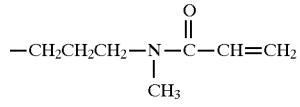

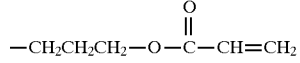

and

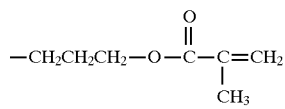

A method for preparation of the acrylamide functional siloxanes useful in the instant invention is taught in U.S. Pat. No. 4,608,270 to Varaprath and 4,861,906 to Varaprath et al., incorporated herein by reference. A method for preparation of the acryloxy and methacryloxy functional siloxanes useful in the instant invention is taught in U.S. Pat. No. 4,568,566 to Toletino, incorporated herein by reference.

The acrylic functional siloxanes described above are useful in hair perming and in other hair treatment applications. In hair perming applications they can be used in addition to or in place of the hydrogen peroxide solution typically used.

The acrylic functional siloxanes, useful in perming applications, are applied to the hair from a suitable delivery means. It is preferable to use a solvent, in particular an alcohol, as the delivery means for the acrylic functional siloxane. Delivery systems such as water, isoparafins, low molecular weight alkanes, silicones, non-polar solvents, propellants, emulsions and others are also useful for application to the hair.

It is preferred to dilute the acrylic functional siloxanes such that they comprise 0.1 to 30 weight percent of the total hair oxidizing composition. The more preferred range is for the acrylic functional siloxane to comprise 1 to 20 weight percent to the total hair oxidizing composition.

The acrylic functional silicones are applied to the hair and reacted using mechanisms such as a catalyst system or radiation. It is theorized that the following reaction takes place on the hair for example, using an acrylamide functional siloxane of formula (IV)

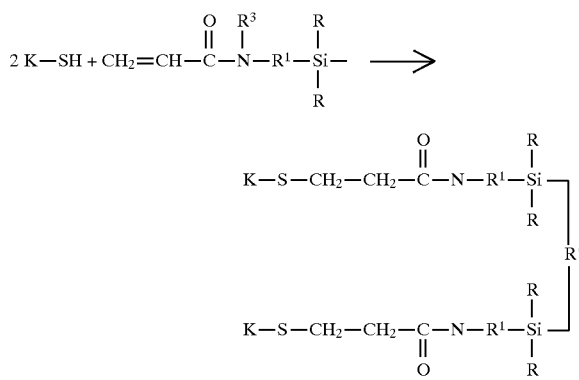

where R" represents the group

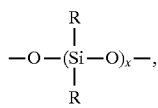

and R, $R^1$, $R^3$ and x are as described above. It is also believed that there is some crosslinking between the C=C groups in the acrylic functionality. Although a true oxidation reaction does not occur with the acrylic functional siloxanes they are stilled referred to a oxidizing agents for descriptive purposes herein.

One mechanism suitable for reacting the acrylic functional siloxane with the hair is with the use of a catalyst system. The use of a catalysts system typically requires the presence of heat. Temperatures from 25° C. to 100°C. are suitable for the reaction to occur. Catalysts suitable for reacting the acrylic functional siloxanes include, but are not limited to, amine types such as triethylamine, triethanolamine, aniline, dimethylaniline, n-butylamine; ferrous containing such as iron oxide; free radical initiators such a hydrogen peroxide, benzoyl peroxide, redox pairs, perborates, percarbonates, acyl peroxides and others. It is preferred that the catalyst comprise 0.01 to 5 weight percent of the total hair oxidizing compositions. The more preferred range is 0.1 to 2 weight percent of the total hair oxidizing compositions.

Another suitable mechanism for reacting the acrylic functional siloxane with the hair is to use radiation such as electron beam and ultraviolet. It is preferred to use ultraviolet (UV) radiation in the presence of a photo-initiator to react the acrylic functional siloxane. Photo-initiators suitable for the reaction include, but are not limited to, benzoin, benzoin alkyl ethers such as methyl, ethyl, isopropyl or isobutyl benzoin ether, acetophenone derivatives such as dialkoxyacetophenone, O,O-dinethoxy-O-phenylacetophenone, 1-hydroxycyclohexylphenyl ketone, 2-hydroxy-2-methyl-1-phenylpropane-1-one, methyl phenyl glyoxylate, 4-benzoylbenzyl-trimethylammonium chloride, O-acyloxime esters such as 1-phenyl-1,2-propanedione-2-(O-ethoxycarbonyloxime), thioxanthane and its derivatives, benzophenone in combination with a chain transfer agent such as a NH group and azo-bis(isobutyronitrile). It is preferred that the photo-initiator comprise 0.01 to 5 weight percent of the total hair oxidizing composition. The more preferred range is 0.1 to 1 weight percent of the total hair oxidizing composition.

The acrylic functional siloxanes on the hair may also be reacted using electron beam radiation. When electron beam radiation is used it is not necessary to add a photo-initiator or catalyst into the hair oxidizing composition.

A summary of the systems described above from which the hair can be oxidized include a catalyst system which comprises the acrylic functional siloxane, a catalyst and the delivery means. The other system is a radiation curable system which comprises the acrylic functional siloxane, the delivery means and optionally a photo-initiator. The hair oxidizing compositions of the instant invention are produced by combining the desired ingredients prior to applying them to the hair.

The hair perming process using an acrylic functional siloxane as an oxidizing agent comprises washing and setting the hair in the desired manner. The hair is then treated with a typical reducing agent, such as a thioglycolate and allowed to stand until sufficient reduction has occurred. Upon reduction the hair is rinsed with water and the acrylic functional siloxane solution is applied to the hair. Depending on the system chosen the hair is then allowed to stand in the presence of heat (catalyst system) or placed in a radiation source for the desired period of time. The hair is then rinsed and styled in the desired manner.

The acrylic functional siloxane solutions can also be used in conjunction with a typical hydrogen peroxide solution. When using them in conjunction with hydrogen peroxide it is possible to add the hydrogen peroxide into the solution containing the acrylic functional siloxane or treat with hydrogen peroxide as an additional step. It is preferable that when using hydrogen peroxide in the acrylic containing solution that the hydrogen peroxide comprises 0.01 to 90 percent of the total hair oxidizing composition. When using hydrogen peroxide in the acrylic functional siloxane solution it is not necessary to add a catalyst since the hydrogen peroxide will function as the catalyst. The hair is treated with the peroxide/acrylic solution in the same manner as if using only the acrylic containing solution.

The acrylic functional siloxane may also be applied as a separate step in the perming process. The hair is reduced using a typical reducing agent, rinsed with water and the acrylic functional siloxane is applied. After the desired treatment is achieved the hair is rinsed and the typical oxidizing agent, such as hydrogen peroxide, is then applied. The hair is then rinsed again and styled in the desired manner.

When the acrylic functional siloxanes are used in place of hydrogen peroxide, they provide a curl to the hair at least equal to that provided by the use of hydrogen peroxide. In addition they provide a heavy conditioning effect to the hair. Because no peroxide is required during the perm is it feasible to perm colored or dyed hair or perm and color the hair simultaneously. Perming without peroxides provides a bona-fide low damage perm.

Because of the unique bonding characteristics in the hair provided by the use of an acrylic functional siloxane instead of a peroxide the effects of the perm will be longer lasting. This is theorized to be caused by the K—S—C— bond, provided when using an acrylic functional siloxane, is believed to be stronger than the K—S—S— bond provided when using hydrogen peroxide. Also, because of the stronger bond provided in the hair, the odor of the perm is reduced because of less possibility of the bond to convert back to a free mercaptan.

Another hair treatment application in which the acrylic functional siloxanes have found particular usefulness is in shampoos. When formulated into a shampoo it is preferable that the acrylic functional siloxane comprise 0.1 to 20 weight percent of the shampoo formulation.

Additional ingredients in the shampoo can comprise one or more delivery means, nonionic surfactants, and detersive surfactants. Optional ingredients in the shampoo formulation can include thickeners, acids to adjust the pH, fragrances, colorants, preserving agents, anti-static agents catalysts, photo-initiators and others. The preferred delivery means for the shampoo formulation is water. It is preferred that water comprise 50 to 95 weight percent of the total shampoo formulation.

Detersive surfactants useful in the shampoo formulation can include, but are not limited to, anionic surfactants such as sodium, ammonium, and triethanolamine salts of lauryl sulfate and lauryl ether sulfate; and amphoterics such as N-coamidopropyl dimethyl glycerine. The detersive surfactant functions as a cleansing and foaming agent in the shampoo and is preferably water soluble. It is preferred that the detersive surfactant comprise 1 to 35 percent by weight of the shampoo formulation.

Nonionic surfactants useful in the shampoo formulation can include, but are not limited to, fatty acid alkanolamides such as isosteraric acid diethanolamide, lauric acid diethanolamide, coconut fatty acid monoethanolamide; and amine oxides such as N-cocodimethylamine oxide, and N-stearyl dimethylamine oxide. Nonionic surfactants solubilize the acrylic functional siloxane polymer into the aqueous solution containing the detersive surfactant. It is preferred that the nonionic surfactant comprise 0.1 to 15 percent by weight of the shampoo formulation.

Thickeners useful in the shampoo formulation can include electrolytes such as sodium chloride; saccharides such as fructose and glucose; gum arabic; cellulose derivatives; and starch and starch derivatives. The thickeners are used to provide a convenient viscosity to the shampoo. In some instances, an anti-static agent, when used, may serve as the thickener. Thickeners may be added in quantities sufficient to provide the desired viscosity.

Nonionic surfactants, detersive surfactants, and thickeners and optional ingredients can be further exemplified by those described in U.S. Pat. No. 4,559,227 to Chandra et al., herein incorporated by reference. Catalysts and photo-initiators useful in the shampoo formulations include those that were described above as being useful in hair oxidizing compositions.

The shampoo is formulated by mixing or whipping together the nonionic surfactant and the acrylic functional siloxane, then adding the detersive surfactant, water and optional ingredients. The shampoo may be in the form of a gel, cream, liquid, paste and others. It is intended to be used by adding the shampoo to the hair, massaging it into the hair, and rinsing with water to remove.

The shampoos of the instant invention containing the acrylic functional siloxane provided some benefits to the hair while wet and also after drying. These benefits include combing, feel and appearance.

It may be possible, in the presence of a catalyst or photo-initiator to react the acrylic functional siloxane on the hair by using heat means such as a dryer or other styling means or through the use of UV radiation such as that from the sun.

Additional hair treatment compositions in which the acrylic functional siloxanes can be incorporated include conditioners, rinses, creams, gels, sprays, foams and others.

So that those skilled in the art can understand and appreciate the invention taught herein, the following examples are presented, it being understood that these examples should not be used to limit the scope of this invention over the limitations found in the claims attached hereto.

EXAMPLE 1

Three (A,B, and C) 2 gram tresses, of European Brown virgin human hair were moistened with water and wound onto standard perming rods and treated with 10 grams of a standard solution of thioglycolic acid. After 30 minutes the tresses were rinsed, while still in the rods, and blotted to remove excess moisture.

Tress A was then soaked for 1 minute in a standard 2.2 percent hydrogen peroxide solution.

Tress B was soaked for 1 minute in a solution consisting of 5 grams of an acrylamide functional siloxane of the formula

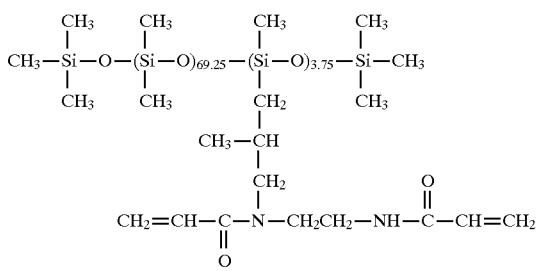

1 gram of triethylamine and 95 grams of ethanol.

Tress C was soaked for 1 minute in a solution consisting of 42.8 grams of the solution used in B an 3.4 grams of 30% aqueous hydrogen peroxide.

All three tresses were then placed in a 40° C. oven for 6 minutes. The tresses were then removed from the rods, thoroughly rinsed with water and hung to dry for a 24 hour period. Tresses B and C were observed to have a wave at least equal to that of A. Tresses B and C were also noted to have durable conditioning. After one shampooing using a blank shampoo, Tresses B and C had a tighter wave than A. They also looked and felt nicer.

EXAMPLE 2

Two (E and F) 2 gram, European Brown tresses of virgin human hair were moistened with water and wound onto standard perming rods and treated with 10 grams of a standard solution of thioglycolic acid. After 30 minutes the tresses were rinsed, while still in the rods, and blotted to remove excess moisture.

Tress E was soaked for 1 minute is a solution consisting of 5.28 grams of an acrylamide functional siloxane of the formula

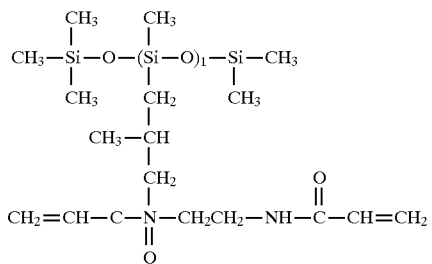

82.9 grams of ethanol and 1.0 grams of triethylamine. The tress was then place in an oven at 40° for 9 minutes.

Tress F was soaked for 1 minute in a solution consisting of 5.12 grams of the acrylamide functional siloxane used in tress E, 87.5 grams of ethanol, and 1 gram of a photo-initiator commonly known as Darocur 1173, manufactured by EM Chemicals, Inc. The tress was then placed under UV radiation for 15 minutes.

Each tress was then removed from the rods, thoroughly rinsed with water and hung to dry for a 24 hour period.

Tresses E and F were shown to have a curl at least equal to that of Tress A (example 1). The hair of tresses E and F were also shown to have a durable conditioning.

EXAMPLE 3

A blank shampoo (I) was formulated by adding 30 grams of ammonium lauryl sulfate to 3 grams of lauramide DEA (lauric acid amide of diethanolamine). 70 grams of water was then blended into the mixture. The pH was adjusted to 5 by using a solution of 50% aqueous citric acid. The shampoo was thickened using 1% by weight of an ammonium chloride solution.

The acrylamide functional siloxane shampoo (II) was formulated by mixing and then "whipping" 2 grams of an acrylamide functional siloxane as used in example 1, and 3 grams of lauramide DEA (lauric acid amide of diethanolamine). 30 grams of ammonium lauryl sulfate and 89 grams of water was added. The pH was adjusted to 5 using a solution of 50% aqueous citric acid. The shampoo was thickened using 1% by weight of an ammonium chloride solution.

Two tresses (F and G) of European brown virgin human hair were shampooed using the blank shampoo and dried.

Tress F was rewet and shampooed with 0.5 grams of shampoo (I). The shampoo was then worked into the hair for 1 minute and rinsed with water for 1 minute. It was detangled using a wide tooth comb (one-pass) and hung up to dry. After 24 hours dry properties were evaluated.

Tress G was rewet and shampooed with 0.5 grams of shampoo (II). The shampoo was then worked into the hair for 1 minute and rinsed with water for 1 minute. It was detangled using a wide tooth comb (one-pass) and hung up to dry. After 24 hours dry properties were evaluated.

The tresses were subjectively evaluated on wet combing, wet feel, dry feel, dry comb and dry appearance. Tress G showed slightly better dry properties and noticeably better wet properties than tress F. The appearance of G was "nicer" than that of F.

What is claimed is:

1. A method for treating hair comprising
    (a) treating the hair with a reducing agent;
    (b) rinsing the treated hair with water;
    (c) applying to the hair a hair oxidizing composition comprising
        (i) 0.1 to 30 weight percent based on the hair oxidizing composition of an acrylic functional siloxane selected from the group consisting of

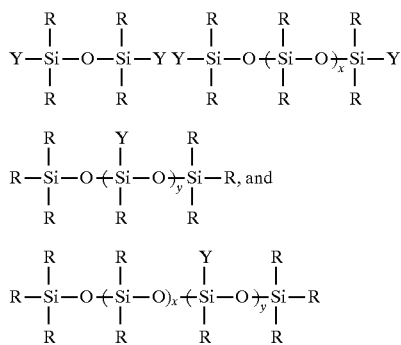

and
        (ii) 0.01 to 5 weight percent based on the total weight of the hair oxidizing composition of a catalyst; and
    (d) allowing the acrylic functional siloxane of (c) to react with the hair by exposing the hair to a source of heat;
    wherein R is independently selected from the group consisting of an alkyl group consisting of 1 to 6 carbon atoms and an aryl group consisting of 6 to 10 carbon atoms;
    Y is independently selected from the group consisting of

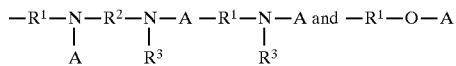

where $R^1$ and $R^2$ are independently selected from the group consisting of straight and branched chain alkylene group consisting of 1 to 10 carbon atoms, and arylene group consisting of 6 to 10 carbon atoms; any of said $R^1$ and $R^2$ groups optionally containing an ether oxygen or any functional substituant, unreactive with hair, within the aliphatic segments thereof;
    $R^3$ is selected from the group consisting of the hydrogen atom, an alkyl group of 1 to 10 carbon atoms and an aryl group consisting of 6 to 10 carbon atoms; and
    A is the group

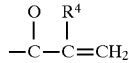

where $R^4$ is selected from the group consisting of the hydrogen atom and the methyl group; and
    x has the value of 1 to 10,000 and
    y has the value of 1 to 100.

2. A method as claimed in claim 1 wherein the acrylic functional siloxane is of the formula

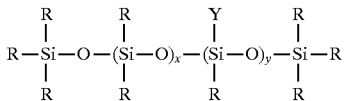

where R is —CH$_3$, Y is the group

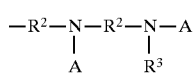

and $R^2$ is the group —CH$_2$CH$_2$—.

3. A method as claimed in claim 1 wherein the acrylic functional siloxane is of the formula

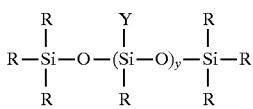

where R is —CH$_3$ , Y is the group

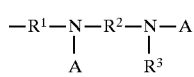

and $R^2$ is the group —CH$_2$CH$_2$—.

4. The method of claim 1 wherein the acrylic functional siloxane is present in a range from 1 to about 20 weight percent of the hair oxidizing composition.

5. The method of claim 1 wherein the acrylic functional siloxane is present in a range from 1 to about 6 weight percent of the hair oxidizing composition.

6. A method for treating hair comprising
(a) treating the hair with a reducing agent;
(b) rinsing the treated hair with water;
(c) applying to the hair a hair oxidizing composition comprising
  (i) 0.1 to 30 weight percent based on the hair oxidizing composition of an acrylic functional siloxane selected from the group consisting of

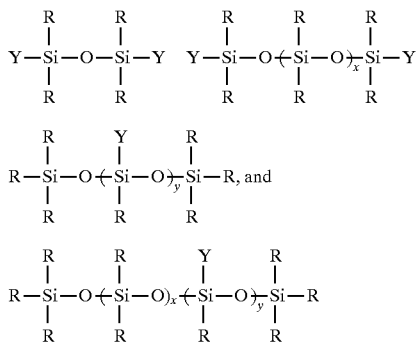

and
  (ii) 0.01 to 5 weight percent based on the hair oxidizing composition of a photo-initiator; and
(d) allowing the acrylic functional siloxane of (c) to react with the hair by exposing the hair to a source of radiation;
wherein R is independently selected from the group consisting of an alkyl group consisting of 1 to 6 carbon atoms and an aryl group consisting of 6 to 10 carbon atoms;
Y is independently selected from the group consisting of

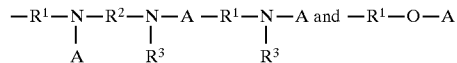

where $R^1$ and $R^2$ are independently selected from the group consisting of straight and branched chain alkylene group consisting of 1 to 10 carbon atoms, and arylene group consisting of 6 to 10 carbon atoms; any of said $R^1$ and $R^2$ groups optionally containing an ether oxygen or any functional substituant, unreactive with hair, within the aliphatic segments thereof;
$R^3$ is selected from the group consisting of the hydrogen atom, an alkyl group of 1 to 10 carbon atoms and an aryl group consisting of 6 to 10 carbon atoms; and
A is the group

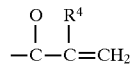

where $R^4$ is selected from the group consisting of the hydrogen atom and the methyl group; and
x has the value of 1 to 10,000 and
y has the value of 1 to 100.

7. The method as claimed in claim 1 wherein the catalyst is selected from the group consisting of amines, ferrous containing catalysts and free radical initiators.
8. The method as claimed in claim 1 wherein the catalyst is triethanolamine.
9. The method as claimed in claim 1 wherein the catalyst is hydrogen peroxide.
10. The method as claimed in claim 1 wherein there is also present in the hair oxidizing composition (iii) a delivery means.
11. The method as claimed in claim 1 wherein the delivery means is selected from the group consisting of solvent, water, isoparafins, low molecular weight alkanes, silicones, non-polar, solvents, propellants and emulsions.
12. The method as claimed in claim 11 wherein the delivery means is an alcohol.
13. The method as claimed in claim 6 wherein the acrylic functional siloxane is of the formula

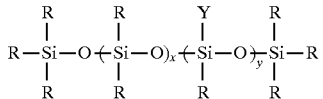

where R is —$CH_3$, Y is the group

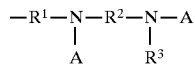

and R2 is the group —$CH_2CH_2$—.
14. The method as claimed in claim 6 wherein the acrylic functional siloxane is of the formula

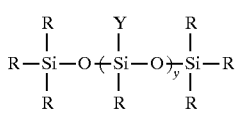

where R is —$CH_3$, Y is the group

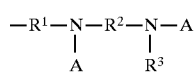

and R2 is the group —$CH_2CH_2$—.
15. The method as claimed in claim 6 wherein the source of radiation is electron beam radiation.
16. The method as claimed in claim 6 wherein there is also present in the hair oxidizing composition (iii) a delivery means.
17. The method as claimed in claim 6 wherein the delivery means is selected from the group consisting of solvent, water, isoparafins, low molecular weight alkanes, silicones, non-polar solvents, propellants and emulsions.
18. The method as claimed in claim 17 wherein the delivery means is an alcohol.

* * * * *